US007008661B2

(12) United States Patent
Koike et al.

(10) Patent No.: US 7,008,661 B2
(45) Date of Patent: Mar. 7, 2006

(54) OIL/FAT COMPOSITION

(75) Inventors: Shin Koike, Tokyo (JP); Takeshi Yasumasu, Tokyo (JP); Tadashi Hase, Tochigi (JP); Takatoshi Murase, Tochigi (JP); Yoshihisa Katsuragi, Tokyo (JP); Akira Takei, Tokyo (JP)

(73) Assignee: Kao Corporation, Tokyo (JP)

( * ) Notice: Subject to any disclaimer, the term of this patent is extended or adjusted under 35 U.S.C. 154(b) by 276 days.

(21) Appl. No.: 10/343,831

(22) PCT Filed: Aug. 7, 2001

(86) PCT No.: PCT/JP01/06778

§ 371 (c)(1),
(2), (4) Date: Feb. 10, 2003

(87) PCT Pub. No.: WO02/11550

PCT Pub. Date: Feb. 14, 2002

(65) Prior Publication Data

US 2003/0198727 A1   Oct. 23, 2003

(30) Foreign Application Priority Data

Aug. 8, 2000   (JP) .............................. 2000-239575

(51) Int. Cl.
A23D 9/007   (2006.01)
(52) U.S. Cl. ..................... 426/601; 426/611; 426/612
(58) Field of Classification Search ........ 426/601–604, 426/606, 608
See application file for complete search history.

(56) References Cited

U.S. PATENT DOCUMENTS

| | | | | |
|---|---|---|---|---|
| 5,686,131 A * | 11/1997 | Sato et al. | ............... | 426/601 |
| 6,159,507 A * | 12/2000 | Igarashi | ............... | 426/2 |
| 6,448,292 B1 * | 9/2002 | Koike et al. | ............... | 514/558 |
| 6,495,536 B1 | 12/2002 | Masui et al. | | |
| 6,762,203 B1 * | 7/2004 | Koike et al. | ............... | 514/546 |
| 6,852,758 B1 * | 2/2005 | Koike et al. | ............... | 514/560 |
| 2001/0036502 A1 * | 11/2001 | Koike et al. | ............... | 426/608 |
| 2004/0052920 A1 * | 3/2004 | Koike et al. | ............... | 426/601 |
| 2004/0062847 A1 * | 4/2004 | Koike et al. | ............... | 426/601 |

FOREIGN PATENT DOCUMENTS

| | | |
|---|---|---|
| EP | 0 953 630 | 11/1999 |
| JP | 63 104917 | 5/1988 |
| JP | 1211305 | * 5/2000 |
| WO | 96 32022 | 10/1996 |
| WO | WO 01/10989 | * 2/2001 |

OTHER PUBLICATIONS

U.S. Appl. No. 10/101,606, filed Mar. 21, 2002, Kataoka et al.
U.S. Appl. No. 10/761,358, filed Jan. 22, 2004, Koike et al.
U.S. Appl. No. 10/343,742, filed Feb. 6, 2003, Koike et al.
U.S. Appl. No. 10/019,427, filed Dec. 31, 2001, Masui et al.
U.S. Appl. No. 10/009,494, filed Apr. 8, 2002, Masui et al.
U.S. Appl. No. 10/857,020, filed Jun. 1, 2004, Moriwaki et al.
M.J. Fishwick et al.: "Quatitative composition of the lpids of cucumber fruit" Journal of the Science of Food and Agriculture, vol. 28, pp. 394-398 1977.
"USDA nutrient database for standard reference, release 13, cucumber", 'Online! United States Dept. of Agriculture, retrieved from the Internet: <URL:http//www.dietobio.com/aliments/en/cucumber.html>, retrieved on Feb. 13, 2002.
Shin Hyo-Sun et al.: "Lipid composition of perilla seed" Journal of the Americal Oil Chemists' Society, vol. 71, No. 6, pp. 619-622 1994.
U.S. Appl. No. 09/926,741, filed Dec. 11, 2001, Kawai et al.
U.S. Appl. No. 09/900,053, filed Jul. 9, 2001, Sugiura et al.
U.S. Appl. No. 09/907,811, filed Jul. 19, 2001, Nakajima et al.
U.S. Appl. No. 09/985,755, filed Nov. 6, 2001, Kudo et al.
U.S. Appl. No. 10/014,356, filed Dec. 14, 2001, Kawai et al.
U.S. Appl. No. 10/101,607, filed Mar. 21, 2002, Suzuki et al.
U.S. Appl. No. 10/120,514, filed Apr. 12, 2002, Sakai et al.
U.S. Appl. No. 10/166,687, filed Jun. 12, 2002, Komatsu et al.
U.S. Appl. No. 10/014,449, filed Dec. 14, 2001, Sakai et al.
U.S. Appl. No. 10/083,387, filed Feb. 27, 2002, Sakai et al.

(Continued)

Primary Examiner—Carolyn Paden
(74) Attorney, Agent, or Firm—Oblon, Spivak, McClelland, Maier & Neustadt, P.C.

(57) ABSTRACT

Provided is an oil/fat composition comprising 10.1 to 94.9 wt. % of a triglyceride, 0.1 to 30 wt. % of a monoglyceride and 5 to 59.9 wt. % of a diglyceride which has, as a fatty acid constituent thereof, 15 to 90 wt. % of an ω3-unsaturated fatty acid having less than 20 carbon atoms. The oil/fat composition of the present invention has excellent heat stability, has body-fat-accumulation resisting action, visceral-fat-accumulation resisting action, blood-sugar-level lowering action, insulin resistance improving action and leptin lowering action and is useful for, as well as pharmaceuticals, preventive or remedial food for diabetes or obesity, and feed.

16 Claims, No Drawings

OTHER PUBLICATIONS

U.S. Appl. No. 10/131,188, filed Apr. 25, 2002, Hase et al.
U.S. Appl. No. 10/259,615, filed Sep. 30, 2002, Sakai et al.
U.S. Appl. No. 10/244,736, filed Sep. 17, 2002, Masui et al.
U.S. Appl. No. 10/238,720, filed Sep. 11, 2002, Hase et al.
U.S. Appl. No. 10/032,493, filed Jan. 2, 2002, Koike et al.
U.S. Appl. No. 10/132,504, filed Apr. 26, 2002, Koike et al.
U.S. Appl. No. 10/061,286, filed Feb. 4, 2002, Koike et al.
U.S. Appl. No. 10/343,748, filed Feb. 6, 2003, Koike et al.

* cited by examiner

OIL/FAT COMPOSITION

TECHNICAL FIELD

The present invention relates to an oil/fat composition having a specific glyceride composition and a specific fatty acid composition, having excellent heat stability, having a body-fat-accumulation resisting action and a visceral-fat-accumulation resisting action, and being extremely useful for health.

BACKGROUND OF THE INVENTION

Lipids (oils or fats), important nutrients in addition to proteins and carbohydrates, are particularly useful as an energy source. It however has a high calorie (9 kcal/g) and intake of it promotes obesity and can be causative of problems such as life-style related diseases. A meal rich in lipids are typically delicious and people of the present day are accustomed to such a meal. In advanced countries under satiation, an increase in lipidic intake has come to be a serious nation-wide problem together with a rise in medical expenses. In recent days, people are highly interested particularly in health promotion and maintenance and preventive treatment of diseases and a number of investigations have been made on the relationship between lipids and obesity or life-style related diseases.

Primary investigations to date have been related to fatty acids constituting a triglyceride, a principal component of a lipid. Nutritionally essential fatty acids are, for example, linoleic acid, arachidonic acid and linolenic acid. These fatty acids are known to be utilized in the body as a constituent of a biomembrane or a raw material of eicosanoids (prostaglandin, thromboxanes, leukotrienes, etc.). In addition, it is reported that there is a high possibility of saturated fatty acids in a diet having a blood-serum cholesterol heightening action, leading to atherosclerosis or heart diseases (Lancet, 2, 959(1950)); and a high linoleic acid oil contained much in a diet increases tumor incidence and size of experimental animals (J. National Cancer Institute, 66, 517(1971)). It is described that an oleic-acid-rich and saturated-fatty-acid-poor diet lowers LDL-cholesterol level, while maintaining an HDL-cholesterol level, thereby reducing the risk of heart diseases (J. Lipid Res., 26, 194(1985), New England J. Medicine, 314, 745(1988)). In addition, physiological activities of various ω3-unsaturated fatty acids including antithrombus effects of eicosapentaenoic acid contained in a fish oil have drawn attention (Ann. Rev. Nutr., 8, 517 (1988)). On the other hand, owing to many double bonds, eicosapentaenoic acid or docosahexaenoic acid involves a problem in stability against oxidation; and eicosapentaenoic acid has an anticoagulant action. Based on the study of intake balance of these fatty acids, a number of research reports have been presented, for example, on a recommendable ratio of saturated fatty acid:mono-unsaturated fatty acid:polyunsaturated fatty acid or a ratio of 6-unsaturated fatty acid: ω3-unsaturated fatty acid. Research is still in progress (Nutrition and Diseases of Oils and Fats", published by Saiwai Shobo, The $6^{th}$ edition of Recommended Dietary Allowances for Japanese", Ministry of Health and Welfare).

With a view to preventing obesity, substitutes for fats and oils or non-absorptive fats and oils have been developed and typical ones include sucrose fatty acid polyester (U.S. Pat. No. 3,600,186). It is excreted without being absorbed in the body so that the calorie derived from fat is 0 kcal/g. There is however a potential problem that it causes anal leakage and inhibits absorption of fat-soluble vitamins. In addition, it is not a supply source of essential fatty acids. The use of this substance was authorized by FDA in 1996, under the restriction that a semi-solid or solid sucrose fatty acid polyester having a melting point of 37.8 to 71.1° C. and containing predetermined amounts of vitamins A, D, E and K can be used only for salty snack foods. This restriction is made for preventing both anal leakage and inhibition of absorption of fat-soluble vitamins. It is reported that a medium-chain fatty acid triglyceride (MCT) is not accumulated on the body, but it has poor heat stability. Similar effects of conjugated linoleic acid, fish oil or perilla oil are disclosed (Lipids, 32, 853(1997), J. Agric. Food Chem., 46, 1225(1998)).

Further disclosed with attention paid to the glyceride structure is an edible oil composition (EP Patent No. 0525, 915), a cholesterol-level lowering agent (Japanese Patent No. 2035495), an agent for lowering the triglyceride concentration in serum (Japanese Patent Application Laid-Open No. 4-300825), a body weight increase inhibitor (Japanese Patent Application Laid-Open No. 4-300826), a preventive or therapeutic agent for fatty liver (Japanese Patent Application Laid-Open No. 4-300828) and a liquid general-purpose oil/fat composition (U.S. Pat. No. 6,004,611). They paid attention only to the effect derived from the diglyceride structure. Although they are free of problems such as anal leakage or inhibition of fat-soluble vitamin absorption, they do not induce effects of diglyceride at the maximum. In addition, when they are used as a processing edible oil, when heated at a high temperature for long hours, thus being exposed to severe conditions, their acid value (AV) tends to show a slight increase.

An object of the present invention is to provide an extremely useful oil/fat composition which has good heat stability, which can be used widely for various purposes, which can prevent obesity due to oils or fats and contributes to good health.

DISCLOSURE OF THE INVENTION

The present inventors have found that a specific oil/fat composition comprising a diglyceride having a specific unsaturated fatty acid constitution has excellent heat stability, and has a body-fat-accumulation resisting action, a visceral-fat-accumulation resisting action, an insulin resistance improving action, blood sugar level lowering action and a leptin lowering action.

The present invention provides an oil/fat composition comprising:
 i) 10.1 to 94.9 wt. % of a triglyceride;
 ii) 0.1 to 30 wt. % of a monoglyceride; and
 iii) 5 to 59.9 wt. % of a diglyceride which contains, as a fatty acid constituent, 15 to 90 wt. % of an 3-unsaturated fatty acid having less than 20 carbon atoms.

DETAILED DESCRIPTION OF THE PREFERRED EMBODIMENTS

The diglyceride to be used in the present invention is required to have, 15 to 90 wt. % (which will hereafter be described % simply), preferably 20 to 80%, more preferably 30 to 70%, especially 40 to 65% of its fatty acid constituents, an ω3-unsaturated fatty acid having less than 20 carbon atoms. The term "ω3-unsaturated fatty acid" as used herein means an unsaturated fatty acid having a first unsaturated bond at the third carbon atom from the ω-position and having a total of at least two unsaturated bonds. Specific examples include α-linolenic acid (all cis-9,12,15-octadecatrienoic acid) and stearidonic acid (all cis-6,9,12,15-octadecatetraenoic acid), with α-linolenic acid being particularly preferred.

The diglyceride containing, as the remaining fatty acid constituent, 10 to 60%, preferably 10 to 50%, especially 12 to 30% of an ω9-unsaturated fatty acid is preferred for marked exhibition of physiological effects, good stability against oxidation and intake balance of fatty acids. Examples of the ω9-unsaturated fatty acid include $C_{10-24}$ ω9-unsaturated fatty acids, preferably $C_{16-22}$ ω9-unsaturated fatty acid, more specifically, oleic acid, eicosamonoenoic acid and docosamonoenoic acid. Of these, oleic acid is particularly preferred. For example, olein-olein diglyceride is preferably contained in an amount less than 45%, more preferably 40% or less from the viewpoint of physiological activity.

Diglyceride preferably contains, as another fatty acid constituent, 2 to 50%, preferably 5 to 40%, more preferably 10 to 30% of a $C_{18-22}$ ω6-fatty acid such as linoleic acid and γ-linolenic acid from the viewpoint of the intake balance of fatty acids and physiologically active effects of a ω3-unsaturated fatty acid. Moreover, from the viewpoint of stability against oxidation and physiologically active effects, a weight ratio of a fatty acid having at least two carbon-carbon double bond/(ω9-unsaturated fatty acid+saturated fatty acid) is preferably 0.7 to 7.5, preferably 1 to 6, more preferably 1.2 to 5, especially 1.5 to 4.

It is preferred for physiological activity that 70 to 100%, preferably 80 to 100%, more preferably 90 to 100% of the fatty acid constituents of a diglyceride is an unsaturated fatty acid having 10 to 24, preferably 16 to 22 carbon atoms.

Such a diglyceride is incorporated in the oil/fat composition of the present invention in an amount of 5 to 59.9%, but from the viewpoints of heat stability and physiological activity, its content is preferably 7 to 55%, more preferably 10 to 50%, especially 15 to 45%.

Fatty acid constituents of the monoglyceride to be used in the present invention are preferred to be similar to those of the diglyceride.

The oil/fat composition of the present invention contains 0.1 to 30% of such monoglyceride. In consideration of taste masking effects, prevention of smoking and heat stability, the content of the monoglyceride is preferably 0.1 to 10%, more preferably 0.1 to 4%, especially 0.1 to 2%, most preferably 0.1 to 1.5%.

The diglyceride and the monoglyceride are preferably incorporated at a relative weight ratio of diglyceride/monoglyceride greater than or equal to 1, preferably 1.5 to 500, especially 2 to 250 from the viewpoints of heat stability and prevention of smoking.

As the fatty acid constituents of the triglyceride, an unsaturated fatty acid is preferably incorporated in an amount of 55 to 100%, more preferably 70 to 100%, still more preferably 80 to 100%, especially 90 to 100% from the viewpoint of exhibition of physiological activity, while an 3-unsaturated fatty acid is preferably incorporated in an amount of 0 to 40%, more preferably 0 to 30, still more preferably 0 to 25%, especially 0 to 20% from the viewpoint of stability against oxidation and intake balance of fatty acids.

In the oil/fat composition of the present invention, such triglyceride is contained in an amount of 10.1 to 94.9%. From the viewpoint of taste masking effects and heat stability, it is preferably contained in an amount of 20 to 92.9%, especially 47 to 89.9%, most preferably 53 to 84.9%.

In all the fatty acid constituents of the oil/fat composition, a fatty acid having at least 4 carbon-carbon double bonds is contained in an amount of 15% or less, preferably 5% or less, especially 2% or less, with the composition substantially free of such a fatty acid being most preferred.

The above-described diglyceride is available by any one of hydrolysis reaction of a linseed oil, perilla oil, soybean oil or rapeseed oil containing an ω3-unsaturated acyl group or monoenoic acyl group, ester exchange reaction of the above-exemplified oil or fat with glycerin, or esterification of a fatty acid derived from such an oil or fat with glycerin. The reacting method may be either one of chemical reaction in the presence of an alkali catalyst or biochemical reaction using an enzyme such as lipase. The triglyceride is available from a vegetable oil such as soybean oil, rapeseed oil, palm oil, sunflower oil, safflower oil, olive oil, sesame oil, rice oil or corn oil, an animal oil such as beef tallow, lard or fish oil, or hardened oil, fractionated oil, ester exchange oil or random ester exchange oil thereof.

The oil/fat composition of the present invention is preferably provided for use after purified through degumming, acid-removing, washing with water, decoloring or deodorizing in consideration of heat stability and taste. The composition contains a free fatty acid (salt) preferably in an amount of 3.5% or less, more preferably 2.5% or less, still more preferably 1.5% or less, especially 1% or less, most preferably 0.5% or less. A peroxide value (POV, Standard Method for the Analysis of Oils, Fats and Derivatives 2.5.2.1 of Japan Oil Chemists' Society) is 10 or less, preferably 7 or less, more preferably 5 or less, especially 3 or less, most preferably 1 or less. The color (10R+Y) as measured by the Lovibond method (Standard Method for the Analysis of Oils, Fats and Derivatives 2.2.1.1 of Japan Oil Chemists' Society 5¼ inch glass cell is used) is 35 or less, preferably 30 or less, more preferably 25 or less, especially 20 or less.

A preferred oil/fat composition of the present invention has a POV of 3 or less, has a color (10R+Y) of 25 or less, and comprises 47 to 89.9% of the triglyceride, 0.1 to 2% of the monoglyceride, 10 to 50% of the diglyceride and 1% or less of a free fatty acid (salt), wherein the diglyceride has, as fatty acid constituents thereof, 30 to 70% of α-linolenic acid, 10 to 50% of oleic acid, 5 to 40% of an ω6-unsaturated fatter acid, a fatty acid having at least two carbon-carbon double bonds/(ω9-unsaturated fatty acid+saturated fatty acid) at a weight ratio of 1.2 to 5, and 80 to 100% of an unsaturated fatty acid; the triglyceride has as its fatty acid constituent 25% or less of an ω3-unsaturated fatty acid and 55 to 100% of an unsaturated fatty acid; and a fatty acid having at least 4 carbon-carbon double bonds is 2% or less in all the fatty acid constituents.

A more preferred oil/fat composition of the present invention has a POV of 1 or less, has a color (10R+Y) of 20 or less, and comprises 53 to 84.9% of the triglyceride, 0.1 to 1.5% of the monoglyceride, 15 to 45% of the diglyceride, and 0.5% or less of a free fatty acid (salt), wherein the diglyceride has, as its fatty acid constituents, 40 to 65% of α-linolenic acid, 12 to 30% of oleic acid, 10 to 30% of an ω6-unsaturated fatty acid, a fatty acid having at least two carbon-carbon double bonds/(ω9-unsaturated fatty acid+saturated fatty acid) at a weight ratio of 1.5 to 4 and 90 to 100% of an unsaturated fatty acid; the triglyceride has, as its fatty acid constituents, 20% or less of an ω3-unsaturated fatty acid and 70 to 100% of an unsaturated fatty acid; and all the fatty acid constituents are free of a fatty acid having at least 4 carbon-carbon double bonds.

The oil/fat composition of the present invention is preferred to contain a phytosterol. The phytosterol is effective for lowering a cholesterol level. The oil/fat composition of the present invention preferably contains a phytosterol in an amount of 0.05% or greater, especially 0.3% or greater. When a commercially available fatty acid obtained by distillation is used as a raw material, the content of the phytosterol in the oil/fat composition lower then that prepared by other methods of purification. In the case of distillation preparation, it is preferred to add the phytosterol to give a content of 0.05% or greater. The content of phytosterol may fall within a range of 0.05% to 1.2%. It may be added as needed in an amount of 1.2% or greater when a higher cholesterol reduction than that brought by the ordinary vegetable oil is intended. Examples of the phytosterol include that in free form such as α-sitosterol, β-sitosterol, stigmasterol, campesterol, α-sitostanol, β-sitostanol, stigmastanol, campestanol and cycloartenol; and that in ester form such as their fatty acid esters, ferulate esters and cinnamate esters.

The oil/fat composition of the present invention may contain an antioxidant. No limitation is imposed on the antioxidant insofar as it is usually employed for foods or pharmaceuticals. Combination of one or more of catechin, tocopherol, vitamin C fatty acid esters, phospholipid and natural antioxidant components is preferred, with catechin being particularly preferred. Examples of the vitamin C fatty acid esters include palmitate esters, stearate esters, while those of the natural antioxidant components include herbs such as rosemary and extracts from the leaves or roots of a peach. The antioxidant is preferably added to the oil/fat composition of the present invention in an amount of 0.01 to 5%, especially 0.05 to 1%.

It is more preferred to add a crystallization inhibitor to the oil/fat composition of the present invention, if necessary, to provide low temperature stability from a loss of transparency.

Examples of the crystallization inhibitor used in the present invention include polyol fatty acid esters such as polyglycerin-condensed ricinoleate esters, polyglycerin fatty acid esters, sucrose fatty acid esters, sorbitan fatty acid esters, polyoxyethylene sorbitan fatty acid esters, and propylene glycol fatty acid esters.

As the polyol fatty acid esters, polyglycerin fatty acid esters, sucrose fatty acid esters and sorbitan fatty acid esters each having an HLB (calculation formula of Griffin) of 4 or less, especially 3 or less are preferred.

The crystallization inhibitor is preferably added to the oil/fat composition of the present invention in an amount of 0.02 to 0.5%, especially 0.05 to 0.2%.

The oil/fat composition thus obtained has excellent physiological activities such as a body-fat-accumulation resisting action, a serum-triglyceride-increase inhibiting action, a visceral-fat-accumulation resisting action, a weight-increase inhibiting action, a liver-function improving action, a blood-sugar-increase inhibiting action, an insulin-resistance improving action and a leptin-increase inhibiting action; it can be used widely for various purposes owing to excellent heat stability; and has excellent taste. Since an 3-unsaturated acyl group exists not as a free fatty acid but as an acyl group constituting the diglyceride, the composition acts even at a low concentration, has an immediate effect, has a good taste and is safe. Such excellent properties make it possible to use the oil/fat composition of the present invention for foods, feeds and pharmaceuticals.

The oil/fat composition of the present invention can be used for an oil/fat-containing food containing the composition as a part of the food. Healthy foods which exhibit a special function, thereby promoting health can be given as one example of such oil/fat-containing foods. Specific examples include capsules, tablets, granules, powders, bakery foods such as bread, cake, cookie, pie, pizza crust and bakery mix, oil-in-water type oil/fat-containing foods such as soup, dressing, mayonnaise, coffee creamer, ice cream and whip cream, water-in-oil type oil/fat-containing foods such as margarine, spread and butter cream, confections, for example, chocolate, caramel, candy, snacks such as potato chips, and dessert, beverages, sauces, barbecue sauces, peanut butter, fry shortening, baking shortening, dough, filling, enrober, meat processed foods such as ham, sausage and hamburger steak, noodles, frozen foods, retort foods, cheese and roux. The above-exemplified oil/fat-containing food can be prepared by adding, in addition to the above-described oil/fat composition, food raw materials ordinarily employed depending on the kind of the food. The amount of the oil/fat composition of the present invention to be added to the food varies depending on the kind of the food, but is usually 0.1 to 100%, preferably 1 to 80%, especially 2 to 80%. It is preferably added in an amount of 0.2 to 50 g, preferably 1 to 25 g, especially, 2 to 15 g, in terms of the oil/fat composition, once or several times a day. It can also be used as a food raw material such as a cooking oil for frying tempura, fries and the like, as well as frizzling.

When a food contains an oil/fat derived from its raw material, a ratio of the oil/fat derived from the raw material to the oil/fat composition of the present invention is preferably 95:5 to 1:99, more preferably 95:5 to 5:95, still more preferably 85:15 to 5:95, especially 40:60 to 5:95.

When the oil/fat composition of the present invention is mixed with another food raw material and provided as an oil/fat-containing processed food, following raw materials can be used. Examples include edible oils or fats, for example, natural animal or vegetable oils or fats, and processed oils or fats obtained by subjecting these natural animal or vegetable oils or fats to ester exchange reaction, hydrogenation or fractionation. Preferred examples include soybean oil, rapeseed oil, rice bran oil, corn oil, palm oil, sunflower oil, safflower oil, olive oil, sesame oil, linseed oil, perilla oil and fish oil, and processed oils or fats thereof. Examples of an emulsifier include various proteins such as egg protein, soybean protein and milk protein, proteins separated therefrom or (partially) decomposed products of these proteins; and sucrose fatty acid esters, sorbitan fatty acid esters, polyoxyethylene sorbitan fatty acid esters, glycerin fatty acid monoesters, polyglycerin fatty acid esters, polyglycerin condensed ricinoleate esters, glycerin organic acid fatty acid esters, propylene glycol fatty acid esters and lecithin, and enzymatically decomposed products thereof. Examples of a stabilizer include polysaccharide thickeners and starches such as xanthane gum, gellan gum, guar gum, carrageenan, pectin, tragacanth gum-n and konjac mannan. In addition, a flavor developing agent such as salt, sugar, vinegar or seasoning, flavoring such as spice and flavor, colorant and antioxidant such as tocopherol or natural antioxidant component can be added.

As oil/fat-containing foods of the present invention, following ones are preferred.

(1) Oil-in-Water Type Oil/Fat-containing Foods

A weight ratio of the oil phase to the water phase is 1/99 to 90/10, preferably 10/90 to 80/20, especially 30/70 to 75/25. The oil phase has a POV of 10 or less, preferably 3 or less, especially 1 or less. The diglyceride content in the oil phase is 5 to 59.9%, preferably 10 to 50%, especially 15 to 45%, while the triglyceride content is 10.1 to 94.9%, preferably 47 to 89.9%, especially 53 to 84.9%. A ratio of the diglyceride content to the monoglyceride content is preferably 1 or greater. The α-linolenic acid content in the fatty acid constituents of the diglyceride is 20 to 80%, preferably 30 to 70%, especially 40 to 65%. The ratio of the content of fatty acid baving at least 2 carbon-carbon double bonds/the content of (ω9-unsaturated fatty acid+saturated fatty acid) is 0.7 to 7.5, preferably 1.2 to 5, especially 1.5 to 4. The content of an ω3-unsaturated fatty acid in the fatty acid constituents of the triglyceride is 40% or less, preferably 25% or less, especially 20% or less. The phytosterol content is 0 to 10%, preferably 1 to 7%, especially 2 to 5%, the emulsifier content is 0.01 to 5%, especially 0.05 to 3%, and the stabilizer content is 0.5%, especially 0.01 o 2%. The pH is 1.0 to 7.0, preferably 2.0 to 6.0, especially 3.0 to 5.0 and can be adjusted with an organic acid (or salt thereof) such as vinegar, citric acid or lemon juice, or an inorganic acid (or salt thereof) such as phosphoric acid (salt thereof).

From the above-described materials, oil-in-water type oil/fat-containing foods such as dressing, mayonnaise, coffee whitener, ice cream, sauce, soup and beverage can be prepared in a conventional manner.

(2) Water-in-Oil Type Oil/Fat-containing Foods

A weight ratio of the water phase to the oil phase is 90/10 to 1/99, preferably 80/20 to 10/90, especially 70/30 to 35/65. The POV in the oil phase is 10 or less, preferably 3 or less, especially 1 or less. The diglyceride content in the oil phase is 5 to 59.9%, preferably 10 to 50%, especially 15 to 45%. The triglyceride content is 10.1 to 94.9%, preferably 47 to 89.9%, especially 53 to 84.9%. A ratio of the diglyceride content to the monoglyceride content is preferably 1 or greater. The α-linolenic acid content in the fatty acid constituents of the diglyceride is 20 to 80%, preferably 30 to 70%, especially 40 to 65%. A ratio of the content of fatty acid having at least 2 carbon-carbon double bonds/the content of (ω9-unsaturated fatty acid+saturated fatty acid) is 0.7 to 7.5, preferably 1.2 to 5, especially 1.5 to 4. The content of an ω3-unsaturated fatty acid in the fatty acid constituents of the triglyceride is 40% or less, preferably 25% or less, especially 20% or less. The phytosterol content is 0 to 10%, preferably 1 to 7%, especially 2 to 5%, while the emulsifier content is 0.01 to 5%, especially 0.05 to 3%.

From the above-described materials, water-in-oil type oil/fat-containing foods such as margarine or spread can be prepared in a conventional manner.

(3) Pocket-Size Oil/Fat-containing Foods

The oil/fat content is 1 to 30%, preferably 1 to 20% and the POV of the oil/fat is 10 or less, preferably 3 or less, especially 1 or less. The diglyceride content in the oil/fat is 5 to 59.9%, preferably 10 to 50%, especially 15 to 45%. The triglyceride content is 10.1 to 94.9%, preferably 47 to 89.9%, especially 53 to 84.9%. A ratio of the diglyceride content to the inonoglyceride content is preferably 1 or greater. The content of α-linolenic acid in the fatty acid constituents of the diglyceride is 20 to 80%, preferably 30 to 70%, especially 40 to 65%. A ratio of the content of fatty acid having at least 2 carbon-carbon double bonds/the content of (ω9-unsaturated fatty acid+saturated fatty acid) is 0.7 to 7.5, preferably 1.2 to 5, especially 1.5 to 4. The content of an ω3-unsaturated fatty acid in the fatty acid constituents of the triglyceride is 40% or less, preferably 25% or less, especially 20% or less. The phytosterol content is 0 to 20%, preferably 1 to 20%, especially 2 to 15%. Carbohydrate such as sucrose, glucose, fructose, maltose, xylitol, sorbitol, erythritol or starch is preferably added in an amnount of 40 to 99%, while a carbonating agent composed of an effervescing agent such as sodium bicarbonate and an acidic agent such as tartaric acid, fumaric acid or citric acid is preferably added in an amount of 0 to 20%, especially 1 to 10%.

Oil/fat-containing pocket-size foods such as tablet, candy, caramel and gummy candy can be prepared in a conventional manner by using the above-described materials. In particular, use of a carbonating agent makes the food melty in the mouth.

(4) Bakery Foods

The oil/fat content is preferably 1 to 40%, especially 5 to 35% and the POV of the oil/fat is 10 or less, preferably 3 or less, especially 1 or less. The diglyceride content in the oil/fat is 5 to 59.9%, preferably 10 to 50%, especially 15 to 45%. The triglyceride content is 10.1 to 94.9%, preferably 47 to 89.9%, especially 53 to 84.9%. A ratio of the diglyceride content to the monoglyceride content is preferably 1 or greater. The content of α-linolenic acid in the fatty acid constituents of the diglyceride is 20 to 80%, preferably 30 to 70%, especially 40 to 65%. A ratio of the content of fatty acid having at least 2 carbon-carbon double bonds/the content of (ω9-unsaturated fatty acid+saturated fatty acid) is 0.7 to 7.5, preferably 1.2 to 5, especially 1.5 to 4. The content of an ω3-unsaturated fatty acid in the fatty acid constituents of the triglyceride is 40% or less, preferably 25% or less, especially 20% or less. The phytosterol content is 0 to 20%, preferably 1 to 20%, especially 1 to 15%. The flour content is 10 to 70%, with 20 to 60% being especially preferred. The bakery food is preferred to contain at least one of hen's whole egg, egg yolk and egg white, and separated or decomposed product thereof in an amount of 0 to 30%, especially 5 to 25%. The salt content is preferably 0 to 2%, especially 0.1 to 1%. The carbohydrate content is 0 to 25%, while the baking powder content is 0 to 1%.

From these materials, bakery foods such as bread, cake, biscuit and cookie can be prepared in a conventional manner.

Examples of the pharmaceutical include orally administrable agents, e.g., solid preparations such as powders, granules, capsules, pills and tablets, liquid preparations such as aqueous preparations, suspensions and emulsions, and gel preparations. Such an orally administrable agent can be prepared by adding, in addition to the oil/fat composition, excipient, disintegrator, binder, lubricant, surfactant, alcohol, water, water-soluble polymer, sweetening agent, taste corrigent and acidifier, each ordinarily employed according to the dosage form of the orally administrable agent. Examples of the orally administrable preparation include platelet aggregation inhibitor. The amount of the oil/fat composition of the present invention to be added to an orally-administrable preparation may differ with its purpose or dosage form, but addition of it in an amount of 0.1 to 100%, preferably 1 to 80%, especially 5 to 80% is usually preferred. As a dose, 0.2 to 50 g, preferably 1 to 25 g, especially 2 to 15 g in terms of the oil/fat composition, is preferably administered once or several portions a day.

Examples of the feed include livestock feed for cow, pig, fowl and sheep, feed for small animals such as rabbit, rat and mouse, feed for fishes such as eel, porgy, yellowtail and shrimp and pet foods for dog, cat, bird and squirrel. Although the amount of the oil/fat composition of the present invention to be added to feed differs depending on the using purpose of the feed, 1 to 30% is usually added, with 1 to 20% being especially preferred.

Having generally described this invention, a further understanding can be obtained by reference to certain specific examples which are provided herein for purposes of illustration only and are not intended to be limiting unless otherwise specified.

EXAMPLES

Example 1

The following oil/fat compositions were prepared. Analyzed results are shown in Table 1.

Oil/Fat Composition 1

Under a nitrogen gas atmosphere, 400 parts by weight of perilla oil (product of Ohta Oil Mill Co., Ltd.), 84 parts by weight of glycerin and 0.2 part by weight of sodium methoxide ($CH_3ONa$) were reacted at 220° C. for 1.5 hours. The reaction mixture was then fractionated by chromatography on a silica gel column (eluting solvent; mixture of hexane and ethyl acetate (first, 100:0, then 90:10, then 80:20 and finally 70:30). After removal of the solvent by evaporation, the residues were mixed again, whereby Oil/fat composition 1 was obtained.

Oil/Fat Composition 2

By using Lipozyme IM" (product of Novo Nordisk Bioindustry), the immobilized lipase preparation, 650 parts by weight of perilla oil fatty acid and 107 parts by weight of glycerin were esterified at 40° C. for 6 hours at 0.07 hPa, followed by the removal of the lipase preparation by filtration. The resulting reaction mixture was then subjected to molecular distillation at 215° C., followed by decoloring, washing with water, and then deodorizing at 215° C. for 2 hours. To 20 parts by weight of the resulting oil/fat composition, 80 parts by weight of rapeseed oil was added, whereby Oil/fat composition 2 was obtained.

Oil/Fat Composition 3

In a similar manner to that employed for the preparation of Oil/fat composition 2 (except for a decrease of the reaction time to 5 hours), 325 parts by weight of perilla oil fatty acid, 325 parts by weight of high-oleic safflower oil fatty acid and 107 parts by weight of glycerin were esterified. After filtration and molecular distillation and washing with water, deodorizing was conducted for 2 hours at 215° C., whereby Oil/fat composition 3 was obtained.

Oil/Fat Composition 4

By using Lipozyme IM", 650 parts by weight of rapeseed oil fatty acid and 107 parts by weight of glycerin were esterified at 0.067 hPa and 40° C. for 5 hours, followed by the removal of the lipase preparation by filtration. After molecular distillation at 235° C. and washing with water, deodorizing was conducted at 235° C. for 1 hour, whereby Oil/fat composition 4 was obtained.

Oil/Fat Composition 2a

Oil/fat composition 2a was prepared by mixing 100 parts by weight of Oil/fat composition 2, 0.02 part by weight of tocopherol (Mix Vitamin E MDE-6000"; product of Yashiro Co., Ltd.), 0.1 part by weight of catechin (Sunkatol No. 1"; product of Taiyo Chemical Co., Ltd.) 0.25 part by weight of rosemary (Harbalox type HT-0 Extract"; product of Kalsec, Inc.), 0.05 part by weight of a phytosterol (Tama Biochemical Co., Ltd.) and 0.1 part by weight of THL-3" (polyglycerin fatty acid ester, HLB=1; product of Sakamoto Yakuhin Kogyo Co., Ltd.).

Oil/Fat Composition 2b

An oil/fat composition 2b was prepared by mixing 100 parts by weight of Oil/fat composition 2, 0.02 part by weight of tocopherol and 0.1 part by weight of catechin and 0.1 part by weight of THL-3".

Oil/Fat Composition 2c

Oil/fat composition 2c was prepared by mixing 100 parts by weight of Oil/fat composition 2, 0.02 part by weight of tocopherol, 0.1 part by weight of catechin, 0.02 part by weight of VCP (vitamin C palmitate; product of Roche, Ltd.), 0.3 parts by weight of a phytosterol and 0.1 part by weight of THL-3".

Oil/Fat Composition 2d

Oil/fat composition 2d was prepared by mixing 100 parts by weight of Oil/fat composition 2, 0.02 part by weight of tocopherol, 0.02 part by weight of VCP" and 2 part by weight of a phytosterol.

TABLE 1

|  |  | Oil/fat composition | | | |
| --- | --- | --- | --- | --- | --- |
|  |  | Invention product | | | Comparative product |
| Oil/fat composition |  | 1 | 2 | 3 | 4 |
| Glycerides composition *1 | TG | 40.6 | 81.9 | 68.3 | 13.5 |
|  | DG | 52.8 | 17.7 | 30.1 | 85.1 |
|  | MG | 6.4 | 0.3 | 1.2 | 1.1 |
|  | FFA | 0.2 | 0.1 | 0.4 | 0.3 |
| Acid value |  | 0.37 | 0.20 | 0.83 | 0.62 |
| POV meq/kg |  | 0.28 | 0.12 | 0.22 | 0.19 |
| Color (10R + Y, Lovibond method) |  | 23.5 | 12.2 | 15.4 | 13.7 |
| DG-constituting fatty acids *2 | C18:3 ($\omega 3$) | 58.9 | 58.0 | 41.6 | 10.5 |
|  | C18:1 ($\omega 9$) | 12.8 | 17.6 | 34.1 | 57.0 |
|  | C20:1 | 0.0 | 0.1 | 0.1 | 1.7 |
|  | C22:1 | 0.0 | 0.0 | 0.0 | 1.0 |
|  | C18:2 ($\omega 6$) | 16.4 | 16.9 | 15.0 | 21.9 |
|  | C16:0 | 5.6 | 5.7 | 6.0 | 3.7 |
|  | C18:0 | 1.5 | 1.7 | 2.6 | 1.8 |
|  | At least 2 double bonds/($\omega 9$ + saturated) | 3.8 | 3.0 | 1.3 | 0.5 |

TABLE 1-continued

|  |  | Oil/fat composition | | | |
|---|---|---|---|---|---|
|  |  | Invention product | | | Comparative product |
| Oil/fat composition |  | 1 | 2 | 3 | 4 |
| TG-constituting fatty acids *2 | C18:3 (ω3) | 58.7 | 12.9 | 39.3 | 10.4 |
|  | C18:1 (ω9) | 12.9 | 56.5 | 35.5 | 57.1 |
|  | C20:1 | 0.0 | 1.6 | 0.1 | 1.7 |
|  | C22:1 | 0.0 | 1.0 | 0.0 | 1.0 |
|  | C18:2 (ω6) | 16.5 | 21.6 | 15.2 | 21.8 |
|  | C16:0 | 5.7 | 4.0 | 6.2 | 3.8 |
|  | C18:0 | 1.5 | 1.8 | 2.6 | 1.8 |

*1: measured by gas chromatography after trimethylsilylation
*2: measured by gas chromatography after methylation

Example 2

In a test tube having a diameter of 20 mm, 20 g of each of the oil/fat compositions thus prepared was charged (after dissolving 0.02 part by weight of tocopherol in 100 parts by weight of the oil/fat composition). The oil/fat compositions in test tubes were heated to 180° C. Distilled water was forcedly added at a rate of 0.1 mL/min through a stainless test tube set in the each of the oil/fat compositions. An increase in the acid value after 6 hours was measured. The said value (AV) was measured by Standard Method of the Analysis of Oils, fats and Derivatives 2.3.1 of Japan Oil Chemists' Society. Results are shown in Table 2.

TABLE 2

|  | Increase in acid valueΔAV |
|---|---|
| Oil/fat composition 1 of the invention | 0.40 |
| Oil/fat composition 2 of the invention | 0.26 |
| Oil/fat composition 3 of the invention | 0.33 |
| Comparative oil/fat composition 4 | 0.67 |

It has been found that the oil/fat compositions 1 to 3 according to the present invention each had excellent heat stability.

Example 3

C57BL/6J male mice aged 7 weeks were divided into 7 groups. After feeding with a diet having the below-described composition for continuous 5 months, they were weighed. The blood was collected from the aorta abdominalis under anesthesia with ether. Blood sugar level, insulin and leptin were measured and results are shown in Table 3 with those of Comparative product 1 set at 100.

TABLE 3

|  | Invention product | | | Comparative Product | | | |
|---|---|---|---|---|---|---|---|
|  | 1 | 2 | 3 | 1 | 2 | 3 | 4 |
| Diet composition (%) | | | | | | | |
| Rapeseed oil | 15.0 | 15.0 | 15.0 | 5.0 | 30.0 | 15.0 | 15.0 |
| Perilla oil | — | — | — | — | — | 15.0 | — |
| Invention oil/fat Composition 1 | 15.0 | — | — | — | — | — | — |
| Invention oil/fat Composition 2 | — | 15.0 | — | — | — | — | — |

TABLE 3-continued

|  | Invention product | | | Comparative Product | | | |
|---|---|---|---|---|---|---|---|
|  | 1 | 2 | 3 | 1 | 2 | 3 | 4 |
| Invention oil/fat Composition 3 | — | — | 15.0 | — | — | — | — |
| Comparative oil/fat Composition 4 | — | — | — | — | — | — | 15.0 |
| Casein | 20.0 | 20.0 | 20.0 | 20.0 | 20.0 | 20.0 | 20.0 |
| Mineral mixture | 3.5 | 3.5 | 3.5 | 3.5 | 3.5 | 3.5 | 3.5 |
| Vitamin mixture | 1.0 | 1.0 | 1.0 | 1.0 | 1.0 | 1.0 | 1.0 |
| Cellulose | 4.0 | 4.0 | 4.0 | 4.0 | 4.0 | 4.0 | 4.0 |
| Starch | 41.5 | 41.5 | 41.5 | 66.5 | 41.5 | 41.5 | 41.5 |
| Body weight | 114 | 118 | 117 | 100 | 132 | 130 | 121 |
| Blood sugar level | 100* | 113 | 111 | 100 | 123 | 120 | 117 |
| Insulin | 121* | 158* | 129* | 100 | 923 | 628 | 474 |
| Leptin | 342* | 505* | 414* | 100 | 1749 | 1287 | 356* |

*$p < 0.05$, significant difference from the diet of Comparative product 2.

Measuring method of blood sugar level: Glucose test-Wako" (product of Wako Pure Chemical Industries)

Measuring method of insulin: iInsulin Measuring Kit" (product of Morinaga Seikagaku Kenkyujo)

Measuring method of leptin: Mouse Leptin Measuring Kit" (product of Morinaga Seikagaku Kenkyujo)

The oil/fat compositions of the present invention each exhibited excellent blood sugar level lowering action, insulin resistance improving action and leptin lowering action.

Example 4

For 12 months, two male adult volunteers took an ordinary meal for which Oil/fat composition 2 had been used as an edible oil (cooking oil). The average intake amount of Oil/fat composition 2 was 12.3 g/person/day, similar to an average intake amount of an edible oil by a Japanese adult. In Table 4, measured results of BMI and body fat ratio, each before and after the test are shown. A lowering tendency was recognized in any item.

Measuring method of body fat ratio: Impedance method

Measuring method of visceral fat: CT scanning method

Measuring method of subcutaneous fat: CT scanning method

TABLE 4

| | | | Before intake | After intake |
|---|---|---|---|---|
| A: 51 years old | BMI | kg/m² | 25.66 | 23.87 |
| | Body fat ratio | % | 25.5 | 23.2 |
| | Visceral fat | cm² | 136 | 112 |
| | Subcutaneous fat | cm² | 135 | 110 |
| | Serum TG | mg/dL | 62 | 49 |
| B: 32 years old | BMI | kg/m² | 24.65 | 24.15 |
| | Body fat ratio | % | 24.5 | 23.5 |
| | Visceral fat | cm² | 84 | 92 |
| | Subcutaneous fat | cm² | 103 | 89 |
| | Serum TG | mg/dL | 86 | 53 |

Example 5

Test was conducted using edible oils to which ALA-DAG had been added in varied amounts. As a test substance, ALA-DAG containing 49% of -linolenic acid was used (Table 5). ALA-DAG was prepared using linseed oil (product of Yoshihara Oil Mill, Ltd.) in the presence of immobilized lipase in accordance with the method of Birgitte, et, al. (JAOCS, 65, 905(1988)). In consideration of an average intake amount of an edible oil according to National Nutrition Survey in 1998, ALA-DAG was added to a daily intake amount, 10 g, of an edible oil. In Dose 1 group, an edible oil (2.5 g oil) obtained by mixing 2.5 g of ALA-DAG and 7.5 g of rapeseed oil was used as 10 g of a test oil, while in Dose 2 group, an edible oil (3.75 g oil) obtained by mixing 3.75 g of ALA-DAG and 6.25 g of rapeseed oil was used. In Control group, on the other hand, an edible oil (Control oil) composed only of TAG obtained by mixing rapeseed oil (product of Nisshin Oil Mills, Ltd) and perilla oil (Ohta Oil Mill Co., Ltd.) and then adjusting the mixture to have a similar fatty acid composition to the oil used in Dose 1 group was used (Table 6). The test substance was supplied in the form of short bread, mayonnaise, dressing or soup prepared using each of the edible oils. Test was conducted on three groups, that is, Control group (TAG), Dose 1 group (2.5 g of ALA-DAG) and Dose 2 group (3.75 g of ALA-DAG).

TABLE 5

Composition of Experimental Lipid

| Fatty acid | ALA-DAG |
|---|---|
| DG Fatty Acid Composition (%) | |
| C14:0 | 0.0 |
| C16:0 | 5.4 |
| C18:0 | 3.4 |
| C18:1 | 19.3 |
| C18:2 | 15.8 |
| C18:3 | 49.0 |
| Others | 7.1 |
| Composition of glycerides | |
| DG | 87.0 |
| TG | 11.5 |
| Others | 1.5 |

TABLE 6

Fatty Acid Composition of Dietary Lipids in Test 1

| Fatty acid | Control oil | 2.5 g Oil | 3.75 g oil |
|---|---|---|---|
| C14:0 | 0.1 | 0.1 | 0.1 |
| C16:0 | 4.6 | 4.5 | 4.6 |
| C18:0 | 2.0 | 2.4 | 2.5 |
| C18:1 | 51.7 | 49.5 | 44.6 |
| C18:2 | 19.5 | 19.3 | 18.8 |
| C18:3 | 20.9 | 21.5 | 25.9 |
| Others | 1.2 | 2.7 | 3.5 |

In conformity with Declaration of Helsinki, the tests were made with a sufficient care under the observation of a doctor after obtaining the approval of Clinical Test Ethics Committee of Kao Corporation.

The tests were made on 66 healthy male adult volunteers (employees of Kao Corporation) who were 35.7 years old and had a body mass index (BMI) of 23.3 (kg/m²), each on average.

They were classified into three groups so that BMI would be almost equal in each of three groups. After intake of a control test diet containing rapeseed oil (10 g/day) for 4 weeks, double blind intake test was conducted for 12 weeks. They were permitted to take the test substance at any time. In consideration of the average total intake amount described in National Nutrition Survey in 1998 (National Nutrition", published by Daiichi Shuppan Publishing Co., Ltd., in 2000), the total oil intake amount/day including the test diet was set at 50±5 g throughout the test term according to the method of Watanabe, et. al. (J. Jpn. Oil Chem. Soc. 47, 47–54(1998)). The body composition data of each group prior to the test are shown in Table 7.

All the subjects were educated to grasp the intake amount of energy and lipids based on the "Standard Tables of Food Composition in Japan, Fourth Revised Edition" (published by Kagawa Nutrition University's Publishing Division, in 2000). Under the guidance of a control dietitian, the energy and lipid amount were written on every menu of a weekday lunch and as a weekday supper, the subjects were served the same meal with energy and lipid amount written on its menu. With regards to the holiday meal, they were instructed to take a meal while considering the lipid amount and energy of the raw materials with reference to "Standard Tables of Food Composition in Japan, Fourth revised Edition". During the test, alcohol intake/day was limited to not greater than an alcohol amount corresponding to beer of a large bottle (633 mL). The subjects recorded details of everyday diet and refreshments in their meal diary. The details of the diet were analyzed using "Standard Tables of Food Composition in Japan, Fourth Revised Edition". The subjects were also instructed to keep, during the test, the amount of exercise equal to that before the test.

TABLE 7

Initial Characteristics of Subjects

| | | ALA-DG | |
|---|---|---|---|
| Indexes | Control | dose 1 | dose 2 |
| Number of Subjects | 22 | 22 | 22 |
| Age (y) | 34 ± 2 | 37 ± 2 | 36 ± 2 |
| Weight (kg) | 69.4 ± 1.5 | 67.7 ± 1.9 | 67.1 ± 1.4 |
| Height (cm) | 172.2 ± 1.3 | 171.0 ± 1.5 | 169.6 ± 1.4 |

TABLE 7-continued

Initial Characteristics of Subjects

| Indexes | Control | ALA-DG dose 1 | ALA-DG dose 2 |
|---|---|---|---|
| Body mass index (kg/m$^2$) | 23.4 ± 0.6 | 23.1 ± 0.5 | 23.4 ± 0.5 |
| Waist circumference (cm) | 82.3 ± 1.8 | 82.5 ± 1.8 | 82.5 ± 1.4 |
| Hip circumference (cm) | 96.3 ± 0.8 | 95.7 ± 1.0 | 94.8 ± 0.7 |
| Waist/Hip ratio | 0.85 ± 0.01 | 0.86 ± 0.01 | 0.87 ± 0.01 |
| Sum of skinfold thickness (mm) | 32 ± 2 | 34 ± 2 | 31 ± 2 |
| Total fat (cm$^2$) | 160.9 ± 21.8 | 177.0 ± 20.1 | 170.2 ± 15.5 |
| Visceral fat (cm$^2$) | 60.5 ± 11.6 | 57.9 ± 8.2 | 61.3 ± 8.7 |
| Subcutaneous fat (cm$^2$) | 100.5 ± 12.5 | 119.2 ± 13.9 | 108.9 ± 10.1 |
| Liver/Spleen CT ratio | 0.99 ± 0.06 | 1.11 ± 0.05 | 1.08 ± 0.03 |

Values are means ± SE

Measurement:

Measurement of Skinfold Thickness and Body Fat Ratio

Skinfold thickness was measured at two sites, that is, the midpoint of the extended side of the upper aim and below point of the shoulder blade in the back in accordance with the caliper method by using Fat-o-meter" manufactured by Takei Scientific Instruments Co., Ltd (ed. By Health Nutrition Information Society, National Nutrition" (1995) (Results of National Nutrition Survey in 1993), published by Daiichi Shuppan Publishing Co., Ltd.).

Abdominal CT Scanning

The CT scanning was conducted at the cross-section at the naval part and at a position permitting the spleen and liver to be on the same cross-section.

In accordance with the method of Tokunaga, et al., (Int. J. Obes., 7, 437(1983)), the total fat area, visceral fat area and subcutaneous fat area were determined from the CT image. From the latter two areas, a V/S ratio (visceral fat area/subcutaneous fat area) was calculated (Clinical Endocrinology, a special summer number, 35(1990); Bulletin of the Physical Fitness Research Institute, 77, 131(1991)). In accordance with the method of Katoh, et al. (Acta hepatologica Japonica, 25, 1097(1984)), a liver/spleen CT ratio was determined. For CT scanning, TCT-300" and X Vision RIAL" of Toshiba Medical Systems Co., Ltd. and PRATICO" of Hitachi Medical Corporation were employed.

The data was indicated by mean±standard error. The body composition data were indicated relative to the data at the initiation of the test set at 100. The paired t-test was employed for comparison between the values at the initiation of the test and the values upon measurement in each group. For comparison between groups, t-test was employed.

In physical examination (Table 8), relative to the initial values before the starting of the tests, a significant decrease in waist circumference, hip circumference, skinfold thickness and subcutaneous fat area and a significant increase in a liver/spleen CT ratio, that is, reduction in liver fat, were recognized in each test group. In Dose 1 and Dose 2 groups, apparent decreases in visceral fat area and subcutaneous fat area relative to the initial values before starting of the test were recognized and these decreases mean a significant difference from the control group.

TABLE 8

Changes in Rate of Variation on Body Indexes

| | Control | | | |
|---|---|---|---|---|
| | 0w | 4w | 8w | 12w |
| Weight | 100 | 99.6 ± 0.2 | 99.4 ± 0.3 | 99.5 ± 0.4 |
| Body mass index | 100 | 99.6 ± 0.2 | 99.4 ± 0.3 | 99.5 ± 0.4 |
| Waist circumference | 100 | 99.4 ± 0.2## | 99.3 ± 0.3 | 98.9 ± 0.4## |
| Hip circumference | 100 | 97.9 ± 0.2## | 98.1 ± 0.2## | 98.3 ± 0.3## |
| Waist/Hip ratio | 100 | 101.5 ± 0.3## | 101.3 ± 0.4## | 100.7 ± 0.3## |
| Skinfold thickness | 100 | 96.3 ± 0.8## | 94.4 ± 1.0## | 92.9 ± 1.5## |
| Total fat area | 100 | 91.9 ± 2.2## | 93.3 ± 2.8# | 98.4 ± 4.0 |
| Visceral fat area | 100 | 94.1 ± 3.8 | 94.0 ± 4.2 | 104.6 ± 6.3 |
| Subcutaneous fat area | 100 | 92.4 ± 2.4## | 94.1 ± 2.7# | 97.2 ± 3.5 |
| Liver/Spleen CT ratio | 100 | 112.0 ± 4.0## | 112.0 ± 4.3# | 108.3 ± 3.6# |

| | dose 1 | | | |
|---|---|---|---|---|
| | 0w | 4w | 8w | 12w |
| Weight | 100 | 98.7 ± 0.4## | 98.4 ± 0.4## | 98.6 ± 0.6# |
| Body mass index | 100 | 98.7 ± 0.4## | 98.4 ± 0.4## | 98.6 ± 0.6# |
| Waist circumference | 100 | 98.3 ± 0.3## | 98.1 ± 0.4## | 97.6 ± 0.5## |
| Hip circumference | 100 | 97.8 ± 0.3## | 97.9 ± 0.2## | 97.9 ± 0.3## |
| Waist/Hip ratio | 100 | 100.5 ± 0.4 | 100.2 ± 0.3 | 99.6 ± 0.4 |
| Skinfold thickness | 100 | 96.4 ± 0.8## | 92.6 ± 1.0## | 91.7 ± 1.3## |
| Total fat area | 100 | 92.7 ± 1.7## | 87.3 ± 2.5##+ | 86.6 ± 4.0##+ |
| Visceral fat area | 100 | 92.2 ± 3.0# | 89.3 ± 3.9#+ | 88.6 ± 4.8#+ |
| Subcutaneous fat area | 100 | 92.9 ± 1.7## | 87.0 ± 2.9##+ | 86.0 ± 4.0##+ |
| Liver/Spleen CT ratio | 100 | 96.8 ± 2.3+ | 108.8 ± 4.8 | 110.1 ± 5.2 |

| | dose 2 | | | |
|---|---|---|---|---|
| | 0w | 4w | 8w | 12w |
| Weight | 100 | 99.0 ± 0.3## | 98.9 ± 0.5# | 98.4 ± 0.5## |
| Body mass index | 100 | 99.0 ± 0.3## | 98.9 ± 0.5# | 98.4 ± 0.5## |
| Waist circumference | 100 | 98.6 ± 0.4## | 98.4 ± 0.5## | 98.1 ± 0.5## |
| Hip circumference | 100 | 98.7 ± 0.6# | 98.3 ± 0.3## | 98.1 ± 0.3## |
| Waist/Hip ratio | 100 | 99.9 ± 0.5+ | 100.2 ± 0.4 | 99.9 ± 0.4 |
| Skinfold thickness | 100 | 96.0 ± 0.8## | 93.0 ± 1.3## | 91.2 ± 1.6## |
| Total fat area | 100 | 92.6 ± 1.8## | 86.6 ± 3.0## | 86.4 ± 3.3##+ |
| Visceral fat area | 100 | 90.8 ± 2.2## | 85.9 ± 4.1## | 85.6 ± 4.8##+ |
| Subcutaneous fat area | 100 | 93.3 ± 2.1## | 87.5 ± 2.8## | 87.1 ± 3.0##+ |
| Liver/Spleen CT ratio | 100 | 101.7 ± 2.1+ | 105.4 ± 2.3# | 108.7 ± 2.5## |

Values are means ± SE
Significantly different from control diet group, +p < 0.05, ++p < 0.01
Significantly different from the value at the start of test, #p < 0.05, ##p < 0.01

Example 6

This test was made under the approval and the administration of Animal Care Committee and Animal Ethics Committee of Kao Corporation. As an experimental animal, C57BL/6J mice (7 week old, male, purchased from CLEA JAPAN/Tokyo) was bred at room temperature of 23±2° C. and relative humidity of 55±10% and under illumination from 7:00 to 19:00. After they were carried in, seven days were spent for habituation. They were weighed and classified into test groups so that average weights of these groups would be substantially equal (n=5/group). They were maintained on food and water ad libitum. Feeding was carried out using a Roden CAFE (product of Oriental Yeast Co., Ltd./Tokyo) and the feed was changed every 2 days. The feed intake amount of each test group (n=5/cage/group) per 24 hours was measured once a week and energy intake amount was determined. Under the above-described conditions, they were bred for 20 weeks.

Test Substance and Raw Materials for Feed

ALA-DG was prepared from perilla oil in the presence of immobilized lipase in accordance with the method of Birgitte, et al. (JAOCS, 65, 905(1988)). Compositions of ALA-DG and SR-oil (mixture of safflower oil and rapeseed oil) are shown in Table 9. In SR-oil, oleic acid and linoleic acid account for 29.1% and 57.8%, respectively, of the fatty acid constituents, while in ALA-DG, -linolenic acid accounts for 60.8% of the fatty acid constituents. The DG and TG contents in the glyceride of ALA-DG are 85.2% and 14.1%, respectively. A ratio of 1,3-diglyceride to 1,2-diglyceride was about 7:3. The lard, sucrose, casein, cellulose, mineral mixture, vitamin mixture and -potato starch were purchased from Oriental Yeast Co., Ltd., while the safflower oil and rapeseed oil were purchased from The Nisshin Oil Mills Ltd.

TABLE 9

Composition of Test Oils (%)

|  | SR-oil[a] | ALA-DG[b] |
|---|---|---|
| Fatty Acid | | |
| 16:0 | 6.0 | 5.7 |
| 18:0 | 2.2 | 1.8 |
| 18:1 | 29.1 | 14.0 |
| 18:2 | 57.8 | 15.9 |
| 18:3 | 2.5 | 60.8 |
| 20:0 | 0.4 | n.d. |
| 20:1 | 0.6 | n.d. |
| 22:0 | 0.3 | n.d. |
| 22:1 | 0.2 | n.d. |
| Others | 0.9 | 1.8 |
| Glycerides | | |
| MG | n.d. | 0.7 |
| DG | 1.1 | 85.2 |
| TG | 97.2 | 14.1 |

[a]safflower oil: rapeseed oil = 70:30
[b]α-linolenic acid rich diglyceride
n.d.; not detected Measurement:

Measurement of Body Weight, Visceral Fat Weight and Liver Weight

During the test, mice were weighed every week. Under fasting for 12 hours after completion of the test, they were anesthetized with ether. They were sacrificed under exsanguination and then anatomized. The visceral fat of each part (epididymal, mesenteric, retroperitoneal and perinephric) and the liver were weighed.

Composition and calorie of the feed are shown in Table 10.

TABLE 10

Composition of Diets in Experiment(%)

| Ingredients | LF[a] | HF[b] | HF + ALA-DG |
|---|---|---|---|
| ALA-DG[c] | — | — | 3.0 |
| SR-oil[d] | 5.0 | 30.0 | 27.0 |
| Sucrose | — | 13.0 | 13.0 |
| Casein | 20.0 | 20.0 | 20.0 |
| Cellulose | 4.0 | 4.0 | 4.0 |
| Mineral mixture[e] | 3.5 | 3.5 | 3.5 |
| Vitamin mixture[f] | 1.0 | 1.0 | 1.0 |
| potato starch | 66.5 | 28.5 | 28.5 |
| Calorie (Kcal/100 g) | 399.7 | 522.2 | 522.2 |

[a]Low-fat diet
[b]High-fat diet
[c]α-linolenic acid rich diglyceride
[d]safflower oil: rapeseed oil = 70:30
[e]AIN-76 prescription
[f]AIN-76 prescription + choline bitartrate (20 g/100 g)

Low-fat feed (LF) contains therein 5% of a lipid, while high-fat feed (HF) contains 30% of a lipid and 13% of sucrose. Per 100 g of the feed the calorie of LF is 399.7 Kcal and that of HF is 522.2 Kcal, indicating that the latter has an about 30% higher calorie than the former. The ALA-DG substituted feed was prepared by substituting 3% of SR-oil of HF with 3% of ALA-DG (10% substitution of total lipid). The feed thus prepared was divided into light-shading packages, each containing the feed for 2 days, and after nitrogen purging, these packages were stored at 4° C.

Results were expressed as mean±standard error. Statistical analysis was carried out by one-way analysis of variance (ANOVA) followed by Fisher's PLSD test, Statistical significance is defined as $p<0.05$.

No significant difference was recognized in the initial body weight among test groups (Table 11).

In Week 20, a weight gain was recognized in each test group. In the ALA-DG substituted group, suppression of a weight gain more than that of the HF group was observed and in weight and weight gain in Week 20, a significant difference from the HF group was recognized.

With regards to the energy intake amount during the test, although a significant difference between LF group and each of HF group and ALA-DG substituted group was recognized, there was no significant difference recognized between the HF group and ALA-DG substituted group.

The visceral fat weight, mesenteric fat weight, retroperitoneal fat weight and perinephric fat weight in the ALA-DG substituted group each showed a significantly low value compared with those of the HF group (Table 11).

With regards to the liver weight, the HF group and ALA-DG substituted group showed a significantly high value compared with the LF group, but no difference was recognized between the HF group and ALA-DG substituted group (Table 11).

TABLE 11

Effects of ALA-DG on body weight, liver weight and visceral-fat weight in Week 20

| | Dietary treatment | | |
|---|---|---|---|
| | LF[a] | HF[b] | HF + ALA-DG[c] |
| Body weight (g) | | | |
| Initial | 22.0 ± 0.6 | 22.5 ± 0.9 | 22.0 ± 0.7 |
| Final | 27.6 ± 1.7*** | 36.4 ± 2.3 | 32.0 ± 37* |
| Gain (20 weeks) | 5.6 ± 1.2*** | 13.8 ± 1.9 | 10.0 ± 3.1* |
| Liver weight (g) | 0.92 ± 0.07*** | 1.25 ± 0.11 | 1.16 ± 0.12 |
| Visceral-fat weight (g) | | | |
| Total | 1.264 ± 0.380*** | 3.180 ± 0.823 | 2.284 ± 0.873 |
| Epididymal | 0.578 ± 0.194*** | 1.620 ± 0.328 | 1.188 ± 0.516 |
| Mesenteric | 0.454 ± 0.101 | 0.874 ± 0.161 | 0.634 ± 0.156* |
| Retroperitoneal | 0.162 ± 0.068*** | 0.488 ± 0.0094 | 0.340 ± 0.151* |
| Perinephric | 0.070 ± 0.022** | 0.198 ± 0.068 | 0.122 ± 0.056* |
| Energy intake (Kcal/cage/day) | 57.4 ± 2.8** | 68.6 ± 1.3 | 66.5 ± 4.2 |

Values are means ± SD
[a]Low-fat diet
[b]High-fat diet
[c]α-linolenic acid rich diglyceride
Significantly different from HF, *p < 0.05, p < 0.01, *p < 0.001

Example 7

Scrambled Egg

To 100 g of the whole egg, 0.5 g of salt and 0.1 g of pepper were added. They were beaten well by chopsticks. In a frying pan (24 cm), 5 g of Oil/fat composition 2a of the present invention was charged and heated (city gas, flow rate: 2.2L/min). Thirty seconds after, the beaten egg was poured into the frying pan. The egg was heated for 20 seconds while stirring with chopsticks. In this manner, scrambled egg was cooked.

Example 8

Soft Capsules

In oval soft capsules, 300 mg of Oil/fat composition 2c of the present invention was encapsulated, whereby soft capsules were prepared.

Example 9

Tablets

The below-described components were mixed and the resulting mixture was compressed into tablets, each 200 mg in weight.

Composition of Tablet:

| | |
|---|---|
| Oil/fat composition 2d of the present invention | 10.0% |
| Corn starch | 44.0 |
| Crystalline cellulose | 40.0 |
| Carboxymethylcellulose calcium | 5.0 |
| Silicic anhydride | 0.5 |
| Magnesium stearate | 0.5 |

Example 10

Oil-Water Separated Dressing

With 25 parts by weight of wine vinegar (product of Nakano Suten), 1.25 parts by weight of salt, 0.3 part by weight of pepper and 0.25 part by weight of mustard were mixed. To the resulting mixture, 45 parts by weight of Oil/fat composition 2b of the present invention was added, whereby an oil-water separated dressing was prepared.

Example 11

Mayonnaise

Composition:

| | |
|---|---|
| Oil/fat composition 2b of the invention | 65.0% |
| Egg yolk | 15.0 |
| Vinegar (acidity: 10%) | 7.0 |
| Refined sugar | 1.0 |
| Sodium glutamate | 0.4 |
| Salt | 0.3 |
| Mustard (powder) | 0.3 |
| Thickener (xanthane gum) | 0.2 |
| Water | 10.8 |

After stirring and mixing the above-described components other than Oil/fat composition 2b of the invention in a homomixer, Oil/fat composition 2b was added dropwise to preliminary emulsify the resulting mixture. The pre-emulsion thus obtained was homogenized further in a homomixer, whereby a mayonnaise was prepared (pH 4.0).

Example 12

Margarine-like Spread

| | parts by weight |
|---|---|
| (Oil phase) | |
| Oil/fat composition 1 of the invention | 33.38 |
| Hardened palm oil (IV = 2) | 4.0 |
| Hardened soybean oil (IV = 43) | 2.0 |
| Monoglyceride | 0.5 |
| Flavor | 0.1 |
| Vitamin E | 0.02 |
| (Water phase) | |
| Distilled water | 58.4 |
| Skim milk | 0.3 |
| Salt | 1.3 |

The above-described oil phase and water phase were prepared, followed by mixing and emulsification in a homomixer. The resulting emulsion was cooled in a conventional manner and plasticized into a margarine-like spread.

Example 13

Tablets (Confection)

| | parts by weight |
|---|---|
| Xylitol | 28.4 |
| Sorbitol | 56.9 |
| Oil/fat composition 2b of the invention | 2.5 |
| Phytosterol (product of Tama Biochemical Co., Ltd.) | 2.5 |
| Flavor (ginger oil) | 1.2 |
| Citric acid | 3.0 |
| Sodium bicarbonate | 5.0 |
| Colorant (turmeric powder) | 0.5 |

After mixing the above-described raw materials, the resulting mixture was ground in a mortar. In a conventional maimer, the resulting grind was compressed into tablets, each 2 g in weight, by a tableting machine (24.5 MPa, 4 seconds).

Example 14

Short Bread

| | parts by weight |
|---|---|
| Weak flour | 350 |
| Strong flour | 150 |
| Refined sugar | 150 |
| Whole egg | 125 |
| Oil/fat composition 2b of the invention | 200 |
| Salt | 2.5 |

Refined sugar, salt and Oil/fat composition 2b of the invention were put into a bowl, followed by stirring by a Hobart mixer. The whole egg was gradually added to the resulting mixture and they were stirred again by the Hobart mixer. A mixture of weak flour and strong flour mixed in advance was added in three portions, followed by stirring by the Hobart mixer. The dough thus prepared was divided into pieces, each 25 g in weight, and filled in a metal mold. After baling in an oven (160° C., 50 minutes), they were released from the mold and allowed to cool down, whereby short breads were prepared.

Example 15

Brioche

| | Parts by weight |
|---|---|
| Strong flour | 100 |
| Whole egg | 50 |
| Oil/fat composition 2b of the invention | 30 |
| Refined sugar | 15 |
| Water | 15 |
| Yeast | 5 |
| Yeast food | 0.1 |
| Skim milk | 4 |
| Salt | 2 |

The above-described raw materials other than Oil/fat composition 2b of the invention were mixed in a Hobart mixer at a low speed for 30 seconds. Oil/fat composition 2b was then added, followed by mixing (for 5 minutes at a low speed and 22 minutes at a medium speed). For fermentation, the dough thus obtained was allowed to rise at 27° C. for 30 minutes and then at low temperature of 5° C. for 15 minutes. The resulting dough was divided into pieces, each 37 g in weight, and they were rounded like a ball. After they were allowed to rise at 33° C. for 60 minutes for fermentation, they were baled in an oven (at 190° C. for 9 minutes), whereby brioches were obtained.

INDUSTRIAL APPLICABILITY

The oil/fat composition of the present invention has excellent heat stability, has body-fat-accumulation resisting action, visceral-fat-accumulation resisting action, blood sugar lowering action, insulin resistance improving action and leptin lowering action and is useful for, as well as pharmaceuticals, preventive or remedial food for diabetes or obesity and feeds.

Obviously, numerous modifications and variations of the present invention are possible in light of the above teachings. It is therefore to be understood that within the scope of the appended claims, the invention may be practiced otherwise than as specifically described herein This application is based on Japanese patent application 2000-239575 filed in the Japanese Patent Office on Aug. 8, 2000, the entire contents of which are hereby incorporated by reference.

The invention claimed is:

1. An oil/fat composition comprising:
   i) 10.1 to 94.9 wt. % of a triglyceride;
   ii) 0.1 to 30 wt. % of a monoglyceride; and
   iii) 5 to 59.9 wt. % of a diglyceride which has, as a fatty acid constituent thereof, 15 to 90 wt. % of an ω3-unsaturated fatty acid having less than 20 carbon atoms and 10 to 60 wt. % of an $C_{10-24}$ ω9-unsaturated fatty acid.

2. An oil/fat composition according to claim 1, wherein said ω3-unsaturated fatty acid having less than 20 carbon atoms is α-linolenic acid.

3. The oil/fat composition according to claim 1 or 2, wherein a weight ratio of said diglyceride to said monoglyceride is greater than or equal to 1 and POV is 10 or less.

4. The oil/fat composition according to any one of claims 1 to 2, which has a POV of 3 or less, has a color (10R+Y) of 25 or less, and comprises 47 to 89.9 wt. % of said triglyceride, 0.1 to 2 wt. % of said monoglyceride, 10 to 50 wt. % of said diglyceride, and 1 wt. % or less of a free fatty acid (salt), wherein said diglyceride has, as fatty acid constituents thereof, 30 to 70 wt. % of α-linolenic acid, 10 to 50 wt. % of oleic acid, 5 to 40 wt. % of an ω6-unsaturated fatty acid, a fatty acid having at least two carbon-carbon double bonds/(ω9-unsaturated fatty acid+saturated fatty acid) at a weight ratio of 1.2 to 5, 80 to 100 wt. % of an unsaturated fatty acid; said triglyceride has, as said fatty acid constituents thereof, 25 wt. % or less of an ω3-unsaturated fatty acid and 55 to 100 wt. % of an unsaturated fatty acid; and the content of a fatty acid having at least 4 carbon-carbon double bonds is 2 wt. % or less in all the fatty acid constituents.

5. The oil/fat composition according to any one of claims 1 to 2, which has a POV of 1 or less, has a color (10R+Y) of 20 or less, and comprises 53 to 84.9 wt. % of said triglyceride, 0.1 to 1.5 wt. % of said monoglyceride, 15 to 45% of said diglyceride, and 0.5 wt. % or less of a free fatty acid (salt), wherein said diglyceride has, as fatty acid constituents thereof, 40 to 65 wt. % of α-linolenic acid, 12 to 30 wt. % of oleic acid, 10 to 30 wt. % of an ω6-unsaturated fatty acid, a fatty acid having at least two carbon-carbon double bonds/(ω9-unsaturated fatty acid+saturated fatty acid) at a weight ratio of 1.5 to 4 and 90 to 100 wt. % of an unsaturated fatty acid; said triglyceride has, as fatty acid constituents thereof, 20 wt. % or less of an ω3-unsaturated fatty acid and 70 to 100 wt. % of an unsaturated fatty acid; and all said fatty acid constituents are free of a fatty acid having at least 4 carbon-carbon double bonds.

6. The oil/fat composition according to any one of claims 1 to 2, which further comprises a phytosterol in an amount of 0.05 wt. % or greater.

7. A feed comprising the oil/fat composition as claimed in any one of claims 1 to 2.

8. A pharmaceutical comprising the oil/fat composition as claimed in any one of claims 1 to 2.

9. A cooking oil comprising the oil/fat composition as claimed in any one of claims 1 to 2.

10. In a method of preparing a food composition comprising a fat or oil, the improvement comprising preparing said food composition with the oil/fat composition as claimed in any one of claims 1 to 2.

11. In a method of cooking a food composition in an oil/fat, the improvement comprising heating a food in the oil/fat composition as claimed in any one of claims 1 to 2.

12. A food comprising the oil/fat composition as claimed in any one of claims 1 to 2.

13. The food according to claim 12, wherein said food is an oil-in-water type oil/fat-containing food.

14. The food according to claim 12, wherein said food is a water-in-oil type oil/fat-containing food.

15. The food according to claim 12, wherein said food is a pocket-size oil/fat-containing food.

16. A food according to claim 12, wherein said food is a bakery food.

* * * * *